United States Patent [19]

Coffee et al.

[11] Patent Number: 5,302,523

[45] Date of Patent: Apr. 12, 1994

[54] TRANSFORMATION OF PLANT CELLS

[75] Inventors: Ronald Coffee, Haslemere; James M. Dunwell, Henley-On-Thames, both of England

[73] Assignee: Zeneca Limited, London, England

[21] Appl. No.: 804,664

[22] Filed: Dec. 11, 1991

Related U.S. Application Data

[63] Continuation-in-part of Ser. No. 541,890, Jun. 21, 1990, abandoned.

[30] Foreign Application Priority Data

Jun. 21, 1989 [GB] United Kingdom .................. 8914232

[51] Int. Cl.$^5$ .............................................. C12N 5/14
[52] U.S. Cl. ............................. 435/172.1; 435/172.3; 435/240.4; 935/52
[58] Field of Search ...................... 541/890; 435/172.3, 435/172.1, 240.4; 935/52, 53; 800/DIG. 56

[56] References Cited

U.S. PATENT DOCUMENTS 4,743,548  5/1988  Crossway et al. ................ 435/172.3

OTHER PUBLICATIONS

Neuhaus, et al (Dec. 1987) Theor Appl Genet 75:30–36.
Neuhaus, et al (1986) The EMBO J. 5(7):1437–1444.
Potrykus (Jun. 1990) Bio/Technology 8:535–542.
Appel et al (Oct. 1988) Proc. Natl. Acad. Sci, USA 85:7670–7674.
Costanzo et al (Nov. 1988) Genetics 120: 667–670.
Fechheimer et al. (Dec. 1987) Proc. Natl. Acad. Sci, USA 84:8463–8467.
"Whiskers", The Condensed Chronical Dictionary, Seventh Edition, Ed. Arthur & Elizabeth Rose, Reinhold Publishing Corp., 1966, p. 1018.
Wu et al, "Infection and Synthesis Rate of Southern Bean Mosaic Virus in Soybean Callus Cells under Selected Cultural Conditions", Phytopathology, vol. 68, pp. 1389–1392, 1978.
Alberts et al, "Special Features of Plant Cells", Molecular Biology of the Cell, Garland Publishing Inc., 2nd Edition, 1983, p. 1099.
Armstrong et al, "Establishment and maintenance of friable, embryogenic maize callus and the involvement of L-proline"Planta, 1985, vol. 164, pp. 207–214.
Kamo et al, "Establishment and characterization of long-term embryognic maize callus and cell suspension cultures", Plant Science, vol. 45, 1986, pp. 111–117.
Cockburn et al, "Simple Rapid Method for Gene Transfer", U.S. Patent Appln. 07/472,538, 1990.
Kaeppler et al, "Silicon carbide fiber-mediated DNA delivery into plant cells", Plant Cell Reports, vol. 9, pp. 415–418, 1990.
Cockburn, "Diligence and Ingenuity Pay Off in a Genetic Engineering Laboratory", 1990 Yearbook of Agriculture, pp. 114–116.
Raloff, "Needling tissues to accept foreign genes", Science News, p. 181, 1990.
Asano et al, "Electroporation-mediated and silicon carbide fiber-mediated DNA delivery in Agrostis alba L. (Redtop)", Plant Science, vol. 79, pp. 247–252, 1991.
Kaeppler et al, "Silicon carbide fiber-mediated stable transformation of plant cells", Theor Appln Genet, vol. 84, pp. 560–566, 1992.
Dunahay, "Nuclear Transformation of *Chlamydomonas reinhardtii* with silicon carbide fibers", J. Phycol., vol. 28, p. 11, Abstract No. 59, 1992.
Brown et al, "Not allowing the dust to settle", Chemistry in Britain, Oct. 1992, pp. 910–915.

*Primary Examiner*—Che S. Chereskin
*Attorney, Agent, or Firm*—Cushman, Darby & Cushman

[57] ABSTRACT

Plant cells are transformed by bringing them into contact with a a multiplicity of needle-like bodies on which the cells may be impaled. This causes a rupture in the cell wall allowing entry of transforming DNA either from a surrounding liquid medium or of DNA previously bound to or otherwise entrapped in the needle-like projections.

6 Claims, No Drawings

TRANSFORMATION OF PLANT CELLS

This is a continuation-in-part of application Ser. No. 07/541,890, filed Jun. 21, 1990, now abandoned the entire contents of which is incorporated herein by reference.

This invention relates to a method of transforming plant cells.

The choice of method for the transformation of plant cells tends to be limited to those which are convenient for the target plant type. As a generalisation, dicotyledonous plants are relatively easy to transform whereas monocotyledonous plants are very difficult, there being only a few techniques available in respect of which success has been reported, and that with very low success rate. There is, therefore, a need to make available new techniques for transformation of monocotyledonous plants, which group includes the agronomically most important cereal crops.

One method which is claimed to transform cereal plant cells is the procedure known as "microinjection" where, under the microscope, a DNA construct is injected from a hollow needle into a target cell. A variant of that procedure is the rupturing of the cell wall with a needle, the DNA being added to the surrounding medium and allowed to diffuse into the cell through the break in the cell wall. This is known as "micropricking". Both of these procedures require a high degree of manipulative skill by the operator and are very time consuming.

An alternative approach which has been proposed abandons the high precision of targeting which is inherent in microinjection and micropricking, in favour of a rapid "pepperpot" approach which enables large numbers of cells to be "hit" in a short time, giving a large number of putative transformants for screening.

In one such approach, solid particles, such as tungsten or gold microspheres, bearing surface-bonded DNA are fired at target tissue at very high velocity, for example under propulsion of an explosive charge. One problem with this technique is the effect of the blast of expanding gas on the target tissue. Another is the difficulty of aiming the projectile shower at a selected area of the target.

An object of the present invention is to provide an improved method for transformation of target cells, particularly plant cells.

According to the present invention there is provided a method of transforming cells comprising contacting the cells with a multiplicity of needle-like bodies so that the cells are impaled upon the said bodies, transforming DNA being either surface-bound to the projections or present in a liquid medium in contact therewith.

In one embodiment of the invention a quantity of the needle-like bodies is added to a liquid suspension of the cells to be transformed and the mixture agitated, for example by stirring, so that the moving cells and bodies interact resulting in penetration of the cell wall of the cells.

One method comprises mixing the DNA and fibre suspension, then adding this mixture to the cell suspension. The final mixture is vortexed together. The cells can then be incubated, and tested for expression of recombinant DNA. It has been found that the efficiency of DNA delivery varies according to the conditions; it is affected by several factors including the following: vortex time; cell suspension type (variation also found by H. F. Kaeppler et al, 1990, Plant Cell Reports, 9, 415-418); cell suspension age; osmolarity of culture medium; type of fibres; number of fibres present; type of DNA construct; concentration of DNA. Other factors which may affect DNA delivery include: the physical mixing methods used; the size, shape and uniformity of the fibres; the topology of the DNA (e.g. linear, supercoiled); the presence of "carrier" DNA alongside the transforming DNA.

In another embodiment of the invention, the impalement of the cells on the projections may be effected under a slowly increasing, and controlled, mechanical force which urges the cells on to a surface bearing upstanding needles-like projections. Force may be applied by compressed gas or by a piston arrangement or by centrifuging the cells on to the said surface.

The surface bearing the needle-like projections may be porous and the cells may be drawn into contact therewith by the application of an attractive force on the remote side of the surface, such as a shock evacuation.

A further method comprises attracting the cells to be transformed on to surface bonded needle-like projections by an attractive electric field. Once located proximate the projections, impalement may be effected by, for example, application of a high-frequency alternating field or, alternatively, by causing an electric discharge from the needle-like projections, which are ideal for creating discharges, to perforate the cells.

Once the cells have been impaled on the projections, they may be retained there for whatever is found to be the optimum time interval to effect entry of the DNA into the cells: thereafter they may be repelled from the projections into a culture medium by application of an electric field of suitable polarity and strength, and the wound allowed to close and cells allowed to replicate.

Yet another method of effecting impalement is to provide a magnetic carrier material to which the cells may be attached and to draw the cells onto the needle-like projections using an attractive magnetic force. The magnetic cells, once drawn onto or near to the microprojections may be treated as described for electric field attraction.

Possible needle-like materials for use in this invention are (a) hollow fibres, in the bore of which DNA may be trapped, which may be surface-bonded in upstanding configuration in the form of a felt or "velvet" type of fabric (b) a metallic plate bearing metallic dendritic crystal growths (c) setacious metals (d) a metal or ceramic whiskers which may be in the form of a mat thereof in which the whiskers may be randomly oriented but with a sufficient number presenting a sharp end to the cells (e) carbon, silicon carbide and like fibres (f) glass fibres and, (g) other elongate crystalline materials. Suitable surface bonded forms may be produced by known techniques such as tufting or flocking which utilize an electrostatic charge to cause fibres to stand on end on a substrate to which they may be attached.

Many fine fibrous materials are known which may be used in this application, for example alumina, silica, titania, zirconia, boron, carbon, compounds such as the carbides, and glass fibre. For use in this invention they may be coated with a biocompatible coating to prevent disadvantageous effects. Indeed the provision of such a coating may be advantageous in that it may provide a surface with which transforming DNA may be more conveniently bound, thus improving delivery of the DNA to the interior of the cell. Suitable such coatings may be synthetic resinous materials, surfactants and soluble benign materials such as alginate or gelatin.

In fundamental principle, this type of transformation utilises a procedure which penetrates the cell wall in a non-lethal manner. Such methods, then, seek to wound but not kill the cells. In investigating possible procedures, it may be assumed that if particular method is capable of killing the cells then by making the treatment less severe the method may be adapted to wound.

The invention will now be described, by way of illustration, in the following Examples.

EXAMPLE 1

Viability of Cells After Fibre Treatment

Two grades of silicon carbide whiskers were used in this Example, 30×0.5 µm and 10×0.3 µm. The whisker samples were washed in three changes of water, sterilised in ethanol and air-dried. Finally the whiskers were placed in a cell culture medium, approximately 100 mg of whiskers per 10 ml of medium, and used as a suspension.

Two suspension maize cell lines, one designated LO56 and the other Black Mexican Sweet corn (BMS), were assessed with respect to the effect of the whiskers on cell viability following vortexing in the presence of the whiskers. A degree of cell mortality in this test is indicative of successful treatment of those cells which survive (similar considerations apply in other techniques such as electroporation).

Initial experiments were performed using LO56 cells in a total volume of 1.75 ml of cell suspension, whiskers and medium (1.0 ml cell suspension, 3 days post culture; 0.5 ml sterile distilled water, to reduce osmolality and 0.25 ml of whisker suspension) using two vortex durations, 90 and 180 seconds. Vortexing was conducted using a standard Gallenkamp (Trade Mark) laboratory vortex mixer in either 10 or 50 ml sterile plastic centrifuge tubes.

Observation of the LO56 cells immediately after treatment suggested that no significant effect on cell integrity had occurred using any of the treatments. FDA viability testing after 20 hours confirmed that this was the case. From previous experience of LO56 in other contexts we were aware that it has particularly rigid cells walls.

The same parameters, i.e. vortex duration and tube size were then tested with BMS cells (one day after sub-culture). The viability of these cells, which are considerably larger than LO56, showed a clear relationship with vortex duration using the 50 ml tubes for mixing. With the 180 second treatment approximately half of the cells were found to have been damaged after 20 hours as determined by FDA fluorescence, compared with the controls. Again, relatively little effect was seen using the 10 ml tubes. This confirms the need for the greater degree of mixing which is permitted by the larger diameter tubes.

A clear association was seen between the cells and whiskers immediately after treatment, with the silicon carbide whiskers being particularly concentrated in the intercellular spaces of cell clusters. Whilst whiskers were seen on the surface of some cells their narrow diameter made it impossible to judge whether cell wall penetration had occurred.

EXAMPLE 2

Demonstration of Transient Expression of DNA After Fibre-Mediated Transformation In order to demonstrate that DNA can be inserted by this method, a further experiment was carried out using BMS and controls and treatments listed in the Table below. Cell viability was measured after 20 hours and a fluorimetric GUS assay after 40 hours after treatment. The values obtained are also shown in Table 1. The most significant result is that for treatment T4 in which GUS expression was twice that of the background (control C5).

TABLE 1

| Test | Whiskers | DNA | Vortex | Time | Viability | GUS |
|------|----------|-----|--------|------|-----------|-----|
| C1   | −        | −   | +      |      | 82        | 2.3 |
| C2   | −        | +   | +      | 90   | 75        | 1.1 |
| C3   | +        | −   | −      |      | 72        | 2.0 |
| C4   | +        | −   | +      | 90   | 74        | 2.0 |
| C5   | +        | −   | +      | 180  | 43        | 2.0 |
| C6   | +        | −   | −      |      | 65        | 2.4 |
| T1   | +        | +   | +      | 90   | 68        | 1.0 |
| T2   | +        | +   | +      | 180  | 59        | 1.6 |
| T3   | +        | +   | +      | 90   | 75        | 1.5 |
| T4   | +        | +   | +      | 180  | 33        | 4.2 |

Tests C1 to C6 are controls and T1 to T4 are the tests of the method of this invention.

A mixture of both the 30×0.5 µm and the 10×0.3 µm silicon carbide whiskers was used in these tests.

DNA was used in the form of a CaMV35S/GUS construct. Cell Viability was measured after 20 hours with FDA and GUS expression is in units of fluorescence/hour/µg protein.

EXAMPLE 3

Fibre-Mediated Transformation

Further experiments to demonstrate fibre-mediated transformation were performed.

A suspension maize cell line designated Black Mexican Sweetcorn (BMS) was used. The suspension was subcultured once a week onto fresh BMS medium containing Murashige and Skoog medium, 2% sucrose, 2 mg/ml 2,4-D and adjusted to pH 5.6 prior to filter sterilising.

Silicon carbide fibres (30 µm×0.5 µm) were sterilised under ultraviolet light, then suspended in sterile water to give a 5% solution.

The DNA construct used was a plasmid designated pAI$_1$gusN, containing the Adh 1 promoter and the β-glucuronidase (GUS) reporter gene. The DNA was in the supercoiled form.

A standard GUS fluorometric assay was used to evaluate the amount of DNA taken up by the cells, and was carried out 48 hours after fibre treatment of the cells. The fluorometric assay used the substrate 4-methyl umbelliferyl glucuronide (NUG) which is cleaved by GUS to release a fluorescent product (4-Mu), measured by a fluorometer. A Bradford protein assay was used to calculate GUS expression, based on standards and controls.

Transformation was carried out as follows: 75 µg of plasmid DNA was vortexed for 10 seconds with 80 µl of the fibre suspension. A cell suspension, consisting of 250 µl of packed 3 day-old BMS cells resuspended in 100 µl sterile water with an osmolarity of 125 mOsM/kg, was then added to the DNA/fibre suspension. This mixture was vortexed together for 60 seconds using a standard desktop vortex mixer at the highest possible speed. The conditions used were those found to be optimal for transforming BMS cells.

After vortexing, the mixture was distributed into 5 welled trays to which 1 ml of conditioned media was added. The trays were incubated at 25° C. for 48 hours before GUS assays were performed.

Four replications for each suspension were tested, and four controls were used:
C1: the untreated cell suspension culture;
c2: cell suspension/fibres/DNA without vortexing;
C3: cell suspension/DNA vortexed without fibres;
C4: vortexed cell suspension/fibres/DNA mixture containing a negative-GUS construct (pCal$_1$catN, containing the CaMV35S promoter and the CAT reporter gene).

All experiments were carried out under sterile conditions.

Results are given in Table 2, and show that the treated cells are expressing the GUS gene.

TABLE 2

| MEAN GUS EXPRESSION OF CONTROLS ($\mu$mol 4 Mu/mg/hr) | MEAN GUS EXPRESSION OF TREATED CELLS ($\mu$mol 4 Mu/mg/hr) | INCREASE OF TREATED CELLS OVER BACKGROUND |
| --- | --- | --- |
| 0.0518 | 1.5417 | 29.7X |

EXAMPLE 4

Effect of Varying Conditions on Fibre-Mediated Transformation

Several experiments were carried out to investigate the conditions which enable successful DNA delivery to cells. The method and conditions described in Example 3 were used, unless otherwise stated. Different factors were varied as follows:

a) Vortex time was varied when mixing the cell/DNA/fibre suspension. For these experiments, the plasmid was pCal$_1$gusN (containing the CaMV35S promoter and the GUS gene), and the method used 25 $\mu$g DNA, 40 $\mu$l fibre suspension, and 5 day-old cells resuspended in BMS medium (osmolarity of 202 mOsm/kg). Results are shown in Table 3. The controls gave a mean background GUS expression of 0.00693 $\mu$mol 4 Mu/$\mu$g protein/hour.

TABLE 3

| VORTEX TIME (seconds) | MEAN GUS EXPRESSION OF TREATED CELLS ($\mu$mol 4 Mu/mg/hr) | INCREASE OF TREATED CELLS OVER BACKGROUND |
| --- | --- | --- |
| 60 | 0.0721 | 10.5X |
| 120 | 0.0504 | 7.3X |
| 240 | 0.0326 | 5.0X | b) Cell cultures of different ages (at different growth stages) were used. For these experiments, the plasmid was pCal$_1$gusN, and the method used 25 $\mu$g DNA, 40 $\mu$l fibre suspension, and cells resuspended in BMS medium. Results are shown in Table 4.

TABLE 4

| AGE OF CELLS (days) | MEAN GUS EXPRESSION OF CONTROLS ($\mu$mol 4 Mu/mg/hr) | MEAN GUS EXPRESSION OF TREATED CELLS ($\mu$mol 4 Mu/mg/hr) | INCREASE OF TREATED CELLS OVER BACKGROUND |
| --- | --- | --- | --- |
| 3 | 0.0333 | 1.01 | 30X |
| 5 | 0.0064 | 0.12 | 19X |
| 7 | 0.0286 | 0.7055 | 24X |
| 10 | 0.0110 | 0.2358 | 21X | c) The volume of the 5% fibre suspension used in the mixture was varied. For these experiments, the method used 25 $\mu$g DNA and cells resuspended in BMS medium. Results are shown in Table 5. The controls gave a mean background GUS expression of 0.0261 $\mu$mol 4Mu/$\mu$g protein/hour.

TABLE 5

| VOLUME OF FIBRE SUSPENSION ($\mu$l) | MEAN GUS EXPRESSION OF TREATED CELLS ($\mu$mol 4 Mu/mg/hr) | INCREASE OF TREATED CELLS OVER BACKGROUND |
| --- | --- | --- |
| 80 | 1.0314 | 39.5X |
| 90 | 0.8242 | 31.6X |
| 100 | 0.7928 | 30.4X |
| 120 | 0.0783 | 3.0X | d) The DNA concentration used in the mixture was varied. For these experiments, the method used cells resuspended in BMS medium. Results are shown in Table 6. The controls gave a mean background GUS expression of 0.0580 $\mu$mol 4Mu/$\mu$g protein/hour.

TABLE 6

| AMOUNT OF DNA ($\mu$g) | MEAN GUS EXPRESSION OF TREATED CELLS ($\mu$mol 4 Mu/mg/hr) | INCREASE OF TREATED CELLS OVER BACKGROUND |
| --- | --- | --- |
| 25 | 1.001 | 17.3X |
| 50 | 1.467 | 25.4X |
| 75 | 1.625 | 28.1X | e) The osmolarity of the culture medium (affecting cell turgidity) used in the mixture was varied. The cell culture was resuspended in BMS medium (202 mOsM/kg), a 1:3 mixture of BMS and water (164 mOsM/kg), or in sterile water (125 mOsM/kg). Results are shown in Table 7. The controls gave a mean background GUS expression of 0.0175 $\mu$mol 4Mu/$\mu$g protein/hour.

TABLE 7

| OSMOLARITY OF CULTURE MEDIUM (mOsM/kg) | MEAN GUS EXPRESSION OF TREATED CELLS ($\mu$mol 4 Mu/mg/hr) | INCREASE OF TREATED CELLS OVER BACKGROUND |
| --- | --- | --- |
| 202 | 0.0932 | 5X |
| 164 | 0.1831 | 10X |
| 125 | 0.2142 | 12X |

The results in Tables 3–7 show that transient expression is successfully achieved under a variety of conditions.

We claim:

1. A method of introducing a nucleic acid into plant cells comprising providing in a liquid medium (i) plant cells suspended therein, (ii) a multiplicity of metal or ceramic whiskers bodies and (iii) a nucleic acid, and subjecting said liquid medium containing the said suspended cells, the said metal or ceramic whiskers bodies and said nucleic acid to physical motion so as to create collisions between said metal or ceramic whiskers and said plant cells whereby said nucleic acid is introduced into said plant cells.

2. A method as claimed in claim 1 in which the cells are cells of a monocotyledonous plant.

3. The method according to claim 1 wherein said plant cells are capable of regeneration into whole plants.

4. The method according to claim 3 wherein said plant cells are regenerable cells of *Zea mays*.

5. A method for introducing a nucleic acid into regenerable cells of *Zea mays* comprising providing in a liquid medium (i) said regenerable cells of *Zea mays* suspended therein, (ii) a multiplicity of silicon carbide whiskers, and (iii) a nucleic acid, and subjecting the said liquid medium containing the said suspended regenerable cells of *Zea mays*, the said silicon carbide whiskers and said nucleic acid to physical motion so as to create collisions between said silicon carbide whiskers and said suspended regenerable cells of *Zea mays* whereby said nucleic acid is introduced into said regenerable cells of *Zea mays*.

6. The method of claim 5 wherein said nucleic acid is a DNA.

* * * * *